US010363215B2

(12) United States Patent
Cosgriff-Hernandez et al.

(10) Patent No.: US 10,363,215 B2
(45) Date of Patent: Jul. 30, 2019

(54) POROUS MICROPARTICLES WITH HIGH LOADING EFFICIENCIES

(71) Applicant: THE TEXAS A & M UNIVERSITY SYSTEM, College Station, TX (US)

(72) Inventors: Elizabeth M. Cosgriff-Hernandez, Richmond, TX (US); Robert Scott Moglia, Midland, MI (US)

(73) Assignee: THE TEXAS A&M UNIVERSITY SYSTEM, College Station, TX (US)

(*) Notice: Subject to any disclaimer, the term of this patent is extended or adjusted under 35 U.S.C. 154(b) by 0 days.

(21) Appl. No.: 15/035,460

(22) PCT Filed: Nov. 7, 2014

(86) PCT No.: PCT/US2014/064643
§ 371 (c)(1),
(2) Date: May 9, 2016

(87) PCT Pub. No.: WO2015/070074
PCT Pub. Date: May 14, 2015

(65) Prior Publication Data
US 2016/0287516 A1 Oct. 6, 2016

Related U.S. Application Data

(60) Provisional application No. 61/901,771, filed on Nov. 8, 2013.

(51) Int. Cl.
*A61K 9/113* (2006.01)
*A61K 9/14* (2006.01)
*A61K 38/18* (2006.01)
*A61K 9/00* (2006.01)
*A61K 9/16* (2006.01)

(52) U.S. Cl.
CPC ........... *A61K 9/113* (2013.01); *A61K 9/0019* (2013.01); *A61K 9/146* (2013.01); *A61K 9/1635* (2013.01); *A61K 38/1875* (2013.01)

(58) Field of Classification Search
CPC .................................................. A61K 9/1635
See application file for complete search history.

(56) References Cited

U.S. PATENT DOCUMENTS

| | | | |
|---|---|---|---|
| 4,522,953 A | 6/1985 | Barby et al. | |
| 5,861,175 A | 1/1999 | Walters et al. | |
| 5,900,437 A | 5/1999 | Mitchell et al. | |
| 6,750,261 B1 | 6/2004 | Clear et al. | |
| 6,750,263 B2 | 6/2004 | Sasabe et al. | |
| 6,759,080 B2 | 7/2004 | Thunhorst et al. | |
| 6,765,029 B2 | 7/2004 | Sasabe et al. | |
| 6,797,735 B2 | 9/2004 | Nagasuna et al. | |
| 6,800,666 B2 | 10/2004 | Hahnle et al. | |
| 6,822,010 B2 | 11/2004 | Fujimaru et al. | |
| 6,828,354 B2 | 12/2004 | Hahnle et al. | |
| 6,846,439 B2 | 1/2005 | Kadonaga et al. | |
| 6,890,963 B2 | 5/2005 | Clear et al. | |
| 6,899,890 B2 | 5/2005 | Kirschner et al. | |
| 7,001,548 B2 | 2/2006 | Sakamoto et al. | |
| 7,053,131 B2 | 5/2006 | Ko et al. | |
| 7,060,287 B1 | 6/2006 | Hubbard et al. | |
| 7,138,436 B2 | 11/2006 | Tan et al. | |
| 7,393,878 B2 | 7/2008 | Desmarais et al. | |
| 7,432,311 B2 | 10/2008 | Mezzenga et al. | |
| 7,820,729 B2 | 10/2010 | Akay et al. | |
| 9,180,094 B2 | 11/2015 | Cosgriff-Hernandez et al. | |
| 2004/0026811 A1* | 2/2004 | Murphy | A61L 27/18 264/41 |
| 2005/0261417 A1 | 11/2005 | Mezzenga et al. | |
| 2007/0191963 A1 | 8/2007 | Winterbottom et al. | |
| 2007/0198086 A1 | 8/2007 | Kuroda et al. | |
| 2007/0213422 A1 | 9/2007 | Collier et al. | |
| 2008/0281003 A1 | 11/2008 | Akay et al. | |
| 2009/0093550 A1 | 4/2009 | Rolfes et al. | |
| 2009/0215913 A1 | 8/2009 | Thies et al. | |
| 2010/0068171 A1 | 3/2010 | Guelcher et al. | |

(Continued)

FOREIGN PATENT DOCUMENTS

CN  1923298 A   3/2007
CN  101066473 A  11/2007
(Continued)

OTHER PUBLICATIONS

Akay, G., et al. "Microcellular polyHIPE polymer supports osteoblast growth and bone formation in vitro," Biomaterials 25 (2004) 3991-4000 copyright 2003.
ASTM International, Standard Test Method for Compressive properties of rigid cellular plastics, D 1621-04, 2004.
Barbetta, A. et al., "Scaffolds Based on Bioplymeric Foams," Adanced Functional Materials, vol. 15, No. 1 Jan. 2005, pp. 118-124.
Barbetta, A., et al. "Tailoring the Porosity and Morphology of Gelatin-Methacrylate PolyHIPE Scaffolds for Tissue Engineering Applications," Langmuir, vol. 21, No. 26, 2005 12333-12341.
Barbetta, A., et al., High internal phase emulstions (HIPEs) containing divinylbenzen and 4-vinylbenyl chloride and the morphology of the resulting polyHIPE materials, Chemical Communications 2000, p. 221-222.

(Continued)

*Primary Examiner* — Gina C Justice
(74) *Attorney, Agent, or Firm* — Foley & Lardner LLP

(57) ABSTRACT

An improved polymer delivery system is described which provides polymeric microparticle compositions and porous microparticles formed therefrom. Pore size, pore architecture as well as particle size are also controllable. In some embodiments, both the polymeric microparticle compositions and porous microparticles formed therefrom encapsulate at least one substance, such as a biologic substance (one having biologic activity and/or compatible with a biologic system). The encapsulation occurs prior to polymerization. The amount of substance that is encapsulated may be controlled by the described methods. Said methods do not emply organic solvents. As such, the fabrication occurs in a solvent-free system.

20 Claims, 5 Drawing Sheets

(56) References Cited

U.S. PATENT DOCUMENTS

| | | |
|---|---|---|
| 2010/0326847 A1 | 12/2010 | Jonschker et al. |
| 2011/0104230 A1 | 5/2011 | Mousa et al. |
| 2011/0160321 A1 | 6/2011 | Merrigan et al. |
| 2013/0287735 A1 | 10/2013 | Cosgriff-Hernandez et al. |

FOREIGN PATENT DOCUMENTS

| | | |
|---|---|---|
| CN | 101322854 A | 12/2008 |
| CN | 101322855 A | 12/2008 |
| CN | 101376038 A | 3/2009 |
| CN | 101507839 A | 8/2009 |
| CN | 101698115 A | 4/2010 |
| CN | 102100925 A | 6/2011 |
| DE | 102008006874 A1 | 8/2009 |
| EP | 0060138 A1 | 9/1982 |
| WO | WO-9919003 A1 | 4/1999 |
| WO | WO-2000034454 A2 | 6/2000 |
| WO | WO-2002090958 A2 | 11/2002 |
| WO | WO-2004004880 A2 | 1/2004 |
| WO | WO-2004005355 A1 | 1/2004 |
| WO | WO-2005004811 A2 | 1/2005 |
| WO | WO-2005047435 A2 | 5/2005 |
| WO | WO-2006053031 A2 | 5/2006 |
| WO | WO-2006055940 A2 | 5/2006 |
| WO | WO-2006118987 A1 | 11/2006 |
| WO | WO-2008019940 A1 | 2/2008 |
| WO | WO-2008149096 A2 | 12/2008 |
| WO | WO-2009026387 A1 | 2/2009 |
| WO | WO-2009033088 A1 | 3/2009 |
| WO | WO-2009066283 A2 | 5/2009 |
| WO | WO-2009068912 A1 | 6/2009 |
| WO | WO-2009073068 A2 | 6/2009 |
| WO | WO-2009095153 A1 | 8/2009 |
| WO | WO-2009150113 A1 | 12/2009 |
| WO | WO-2010100506 A2 | 9/2010 |
| WO | WO-2011065987 A1 | 6/2011 |
| WO | WO-2011075183 A1 | 6/2011 |

OTHER PUBLICATIONS

Bhatia, S. N., et al., Tissue engineering at the micro-scale, Biomedical Microdevices 1999;2:131-144.
Binks, B.P., et al., "Inversion of Silica-Stabilized Emulsions Induced by Particle Concentration," Langmuir, vol. 21, No. 8, 2005 pp. 3296-3302.
Binks, B.P., et al., "Influence of Particle Wettability on the Type and Stability of Surfactant-Free Emulsions," Langmuir 2000, vol. 16, No. 23, 8622-8631.
Binks, B.P., et al., "Pickering Emulsions Stabilized by Monodisperse Latex Particles: Effects of Particle Size," Langmuir, vol. 17, No. 15, 2001, 4540-4547.
Binks, Bernard P., et al., "Colloidal Particles at Liquid Interfaces," Chapter 6 entitled Solids-Stablized Emulsions: A Review, Robert J.G. Lopetinsky, et al., 2006, pp. 186-224.
Bokhari, M.A., et al. "Polyhipe Polymer: A Novel Scaffold for In Vitro Bone Tissue Engineering," Advances in Experimental Medicine and Biology, Tissue Engineering, Stem Cells and Gene Therapies, 2003, pp. 247-254.
Bruder, Scott P., et al. "Mesenchymal Stem Cells in Bone Development, Bone Repair, and Skeletal Regeneration Therapy," Journal of Cellular Biochemistry, 56:1994, pp. 283-294.
Burdick, Jason A., et al., "Photoencapsulation of osteoblasts in injectable RGD-modified PEG hydrogels for bone tissue engineering," Biomaterials 23 (2002), pp. 4315-4323.
Busby, W., et al., Tissue engineering matrixes by emulsion templating, Polymer International 2002;51:871-881.
Busby, Wendy, et al., Emulsion-Derived Foams (PolyHIPEs) Containing Poly(-caprolactone) as Matrixes for Tissue Engineering, Biomacromolecules 2001, vol. 2, No. 1, pp. 154-164.
Cameron, High internal phase emulsion templating as a route to well-defined porous polymers, Feb. 14, 2005, Polymer, 46(5): 1439-1449.
Cameron, N.R., et al., "Study of the formation of the open-cellular morphology of poly(styrene/divinylbenzene) polyHIPE materials by cryo-SEM," Colloid & Polymer Science, vol. 274, No. 6 (1996), pp. 592-595.
Cameron, Neil R., et al., "Chemical modification of momlithic poly(styene-divinylbenzen) PolyHIPE materials," Journal of Materials Chemistry, 1996 6(5), pp. 719-726.
Cameron, Neil R., et al., "Synthesis and Characterization of Poly(aryl ether sulfone) PolyHIPE Materials," Macromolecules, vol. 30, No. 19, 1997 pp. 5860-5869.
Cameron, Neil R., et al., "The influence of porogen type on the porosity, surface area and morphology of poly(divinylbenzene) PolyHIPE foams," Journal of Materials Chemistry, 2000, 10, pp. 2466-2471.
Carnachan, Ross J., et al., "Tailoring the morphology of emulsion-templated porous polymers," The Royal Society of Chemistry, Soft Matter, vol. 2 (2006) pp. 606-618.
Christenson, Elizabeth M. et al., "Biodegradable Fumarate-Based PolyHIPEs as Tissue Engineering Scaffolds," Biomacromolecules 2007, 8 3806-3814.
Christenson, Elizabeth M., et al., "Biodegradable Fumarate-Based PolyHIPEs as Tissue Engineering Scaffolds," Biomacromolecules, vol. 8, No. 12. (2007), pp. 3806-3814.
Cohen, N., et al., Synthesis of emulsion-templated porous polyacrylonitrile and its pyrolysis to porous carbon monoliths, Polymer 2011;52:282-287.
Colver, Patrick J., et al., "Cellular Polymer Monoliths Made via Pickering High Internal Phase Emulsions," Chemistry of Materials, vol. 19, No. 7, (2007), pp. 1537-1539.
David, Dganit, et al., "Porous Polyurethanes Synthesized within High Internal Phase Emulsions," Journal of Polymer Science: Part A: Polymer Chemistry, 2009, pp. 5806-5814.
Freyman, T. M., et al., Cellular materials as porous scaffolds for tissue engineering, Progress in Materials Science 2001;46:273-282.
Gokmen et al. Fabrication of Porous "Ciickable" Polymer Beads and Rods through Generation of High Internal Phase Emulsion (HIPE) Droplets in a Simple Microfluidic Device.; Macromolecules 42: 9289-9294, 2009. [retrieved on Dec. 31, 2014]. Retrieved from the Internet.; <URL:; http://www.talhagokmen.com/wp-content/uploads/2011/05/Gokmen_Fabrication-of-Porous-%E2%80%9CCiickable%E2%80%9D-Polymer-Beads-and-Rods-through-Generation-of-High-Internal-Phase-HIPE-Droplets-in-a-Simple-Microfluidic-Device.pdf>. entire document.
Gurevitch, Inna, et al., "Polymerized Pickering HIPEs: Effects of Synthesis Parameters on Porous Structure," Journal of Polymer Science: Part A: Polymer Chemistry, vol. 48, (2010), pp. 1516-1525.
Hacker, M., et al., Solid lipid templating of macroporous tissue engineering scaffolds, Biomaterials 2007;28:3497-3507.
Harris, L. D., et al., Open pore biodegradable martrices formed with gas foaming, Journal of Biomedical Materials Research 1998;42:396-402.
Hayman, M. W., et al., Enhanced neurite outgrowth by human neurons grown on solid three-dimensional scaffolds, Biochemical and Biophysical Research Communications 2004;314:483-488.
Hayman, M. W., et al., Growth of human stem cell-derived neurons on solid three-dimensional polymers, Journal of Biochemical and Biophysical Methods 2005;62:231-240.
Ikem, Vivian O., et al., "High Internal Phase Emulsions Stablized Solely by Functionalized Silica Particles," Angewandte Chemie-International Edition, 2008 47(43), pp. 8401-8403.
International Search Report and Written Opinion for Co-Pending PCT Application No. PCT/US2014/064643 dated Feb. 19, 2015, 9 pgs.
International Preliminary Report on Patentability for Co-Pending PCT Application No. PCT/US2014/064643 dated May 19, 2016, 8 pgs.
Jabbari, Esmaiel, et al., "Synthesis, Material Properties, and Biocompatibility of a Novel Self-Cross-Linkable Poly(caprolactone fumarate) as an Injectable Tissue Engineering Scaffold," Biomacromolecules, vol. 6, No. 5 (2005), pp. 2503-2511.
Karageorgiou, V., et al., Porosity of 3D biomaterial scaffolds and osteogenesis, Biomaterials 2005;26:5474-5491.

(56) References Cited

OTHER PUBLICATIONS

Kenley, R. A., et al., Biotechnology and bone graft substitutes, J. Pharmaceutical Research 1993;10(10):1393-1401.
Kim, Taek Kyoung, et al., "Gas foamed open porous biodegradable polymeric microspheres," Biomaterials 27 (2006), pp. 152-159.
La Gatta, Annalisa, et al., "A Novel Injectable Poly (e-caprolactone)/Calcium Sulfate System for Bone Regeneration: Synthesis and Characterization," Macromolecular Bioscience 2005, 5, 1108-1117.
Landgraf, William, et al., "New Polymer Enables Near Zero-Order Release of Drugs," Zero-Order, vol. 5, No. 2, Feb. 2005.
Langer, R., et al., Tissue engineering, Science 1993;260:920-926.;
Lin-Gibson, S., et al., Systematic investigation of porogen size and content on scaffold morphometric parameters and properties, Biomacromolecules 2007;8:1511-1518.
Lepine, O., et al., "Preparation of macrocellular PU-PS interpenetrating networks," Polymer 46 (2005) 9653-9663.
Lin-Gibson, S., et al., Systematic investigation of porogen size and content on scaffold morphometric parameters and properties, Biomacromolecules 2007;8:1511-1518.
Liu, X., et al., Polymeric scaffolds for bone tissue engineering, Annals of Biomedical Engineering 2004;32(3):477-486.
Lumelsky, Yulia, et al., "Biodegradable Porous Polymers through Emulsion Templating," Macromolecules, vol. 42, No. 5, 2009, pp. 1627-1633.
Maeda, Hayata, et al., "Pickering-Type Water-in-Oil-in-Water Multiple Emulsions toward Multihollow Nanocomposite Microspheres," Langmuir 2010, 26(17) pp. 13727-13731.
Menner, Angelika, et al., "High internal phase emulsion templates solely stabilised by functionalised titania nanoparticles," Chemical Communications, 2007 (41), pp. 4274-4276.
Menner, Angelika, et al., "Particle-Stabilized Surfactant-Free Medium Internal Phase Emulsions as Templates for Porous Nanocomposite Materials: poly-Pickering-Foams," Langmuir, vol. 23, No. 5, 2007, pp. 2398-2403.
Mikos, A. G., et al., Formation of highly porous biodegradable scaffolds for tissue engineering, Electronic Journal of Biotechnology 2000;3(2):114-119.
Misty, A. S., et al., Fabrication and in vitro degradation of porous fumarate-based polymer/alumoxane nanocomposite scaffold for bone tissue engineering, Journal of Biomedical Materials Research Part A 2008;89A:68-79.
Mistry, Amit S., et al, "Fabriation and in vitro degradation of porous fumarate-based polymer/alumoxane nanocomposite scaffolds for bone tissue engineering," Journal of Biomedical Materials Research Part A, 2009, pp. 68-79.
Mistry, Amit S., et al. "In vivo bone biocompatibility and degradation of porous fumarate-based polymer/alumoxane nanocomposites for bone tissue engineering," Journal of Biomedical Materials Research Part A, 2010, pp. 451-462.
Moglia, Robert S., et al.; Injectable PolyHIPEs as High-Porosity Bone Grafts; Biomacromolecules, American Chemical Society Publications, Jun. 27, 2011 (pp. A-H).
Molinspiration Cheminformatics, Cheminformatics on the Web, http://www.molinspiration.com/, accessed 2016, 1 pg.
Notification of Transmittal of the International Search Report and the Written Opinion of the International Searching Authority, including the International Search Report, and the Written Opinion of the International Searching Authority, dated Feb. 17, 2015, 15 pages.
Peter, S. J., et al., In Vitro degradation of a poly(propylene fumarate)/beta-tricalcium phosphase composite orthopaedic scaffold, Tissue Engineering 1997,;3(2):207-215.
Peter, Susan J., et al., "Crosslinking characteristics of an injectable poly9propylene fumarate/β-tricalcium phosphate paste and mechanical properties of the crosslinked composite for use as a biodegradable bone cement," Journal of Biomedical Materials Research, 1999, pp. 314-321.
Peter, Susan J., et al., "Marrow stromal osteoblast function on a poly(propylene fumarate/β-tricalcium phosphate biodegradable orthopaedic composite," Biomaterials, vol. 21, 2000, pp. 1207-1213.
Pham, Q. P., et al., Electrospining of polymeric nanofibers for tissue engineering application: A review, Tissue Engineering 2006;12(5):1197-1211.
Rose, F. R. A. J., et al., Bone Tissue Engineering: Hope vs. Hype, Biochemical and Biophysical Research Communications 2002;292:1-7.
Sikavitsas, V. I., et al., Biomaterials and bone mechanotransduction, Biomaterials 2001;22:2581-2593.
Svaldi Muggli, D., et al., Crosslinking polyanhydrides for use in orthopedic applications: Degradation behavior and mechanics, Journal of Biomedical Materials Research 1999;46:271-278.
Tai, H., et al., Organic-inorganic networks in foams from high internal phase emulsion polymerizations, Polymer 2001;42:4473-4482.
Timmer, Mark D., et al., "Effect of physiological temperature on the mechanical properties and network structure of biodegradable poly-(propylene fumarate)-based networks," Journal of Biomaterial Science Polymer Edition, 2003, pp. 369-382.
Umez-Eronini, N.O., et al., "Optimisation of Bladder Stromal Culture on Polyhipe," European Cells and Materials, vol. 4, Suppl. 2, 2002, pp. 77-78.
Vignati, Emanuele, et al., "Pickering Emulsions: Interfacial Tension, Colloidal Layer Morphology, and Trapped-Particle Motion," Langmuir, vol. 19, No. 17, 2003, pp. 6650-6656.
Williams, Joel M., et al., "Emulsion Stability and Rigid Foams from Styrene or Divinylbenzene Water-in-Oil Emulsions," Langmuir, vol. 6, No. 2, 1990, pp. 437-444.
Williams, Joel M., et al., "High Internal Phase Water-in-Oil Emulsions: Influence of Surfactants and Cosurfactants on Emulsion Stability and Foam Quality," Langmuir, vol. 7, No. 7, 1991, pp. 1370-1377.
Williams, Joel M., et al., "Spatial Distribution of the Phases in Water-in-Oil Emulsions. Open and Closed Microcellular Foams from Cross-Linked Polystyrene," Langmuir, vol. 4, No. 3, 1988, pp. 656-662.
Wong. Bead Based Microreactors for Sensing Applications, Dissertation, The University of Texas at Austin. 1-213, 2007. [retrieved on Dec. 31, 2014]. Retrieved from the Internet. <URL:; https://www.lib.utexas.edu/etd/d/2007/wong)40561/wong)40561.pdf>. pp. 53-62 and 82-85.
Youssef, Carlos, et al., "Preparation of Amazingly Hard polyHIPE material from a Direct Emulsion," Materials Research Society Symposium, 2010, pp. 1-6.
U.S. Appl. No. 15/024,335, Non-Final Office Action, dated Sep. 27, 2018, 16 pgs.
Kovacic, et al., Highly Porous Open-Cellular Monoliths from 2-Hydroxyethyl Methacrylate Based High Internal Phase Emulsions (HIPEs): Preparation and Void Size Tuning, Macromolecules, vol. 40, 2007 (Year: 2007), pp. 8056-8060.
U.S. Appl. No. 15/024,335, filed Mar. 23, 2016, Fast Curing Porous Materials and Control Thereof.
U.S. Appl. No. 15/024,335, Final Office Action, dated May 1, 2019, 18 pgs.

* cited by examiner

FIG. 2
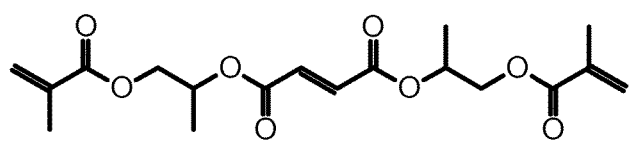
FIG. 3
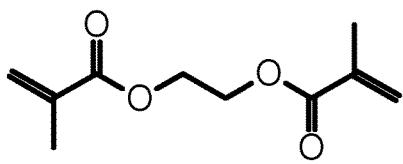
FIG. 4
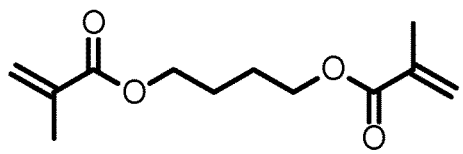
FIG. 5
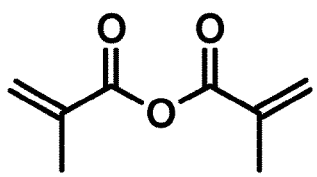
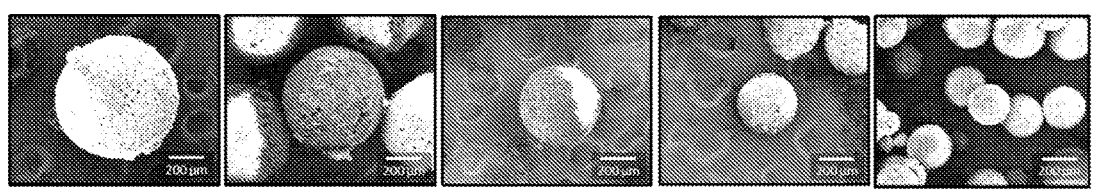
FIG. 6A     FIG. 6B     FIG. 6C     FIG. 6D     FIG. 6E FIG. 7
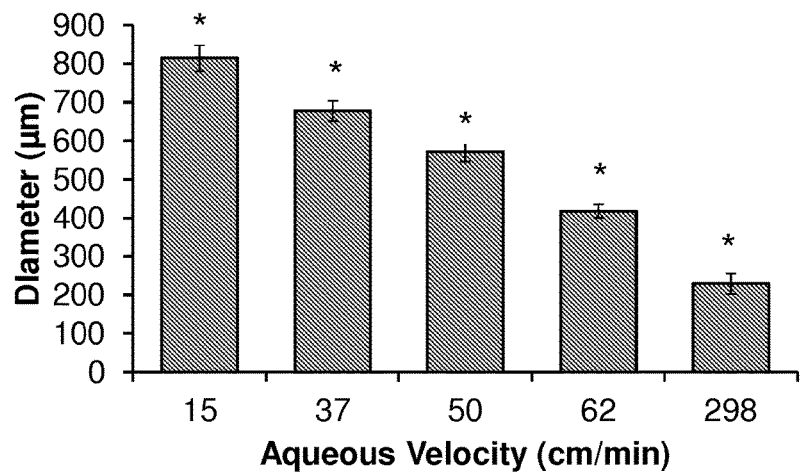
FIG. 8A  FIG. 8B  FIG. 8C
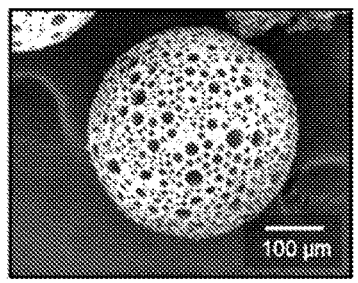 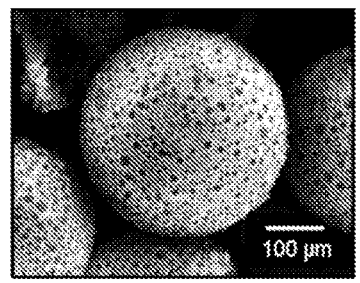 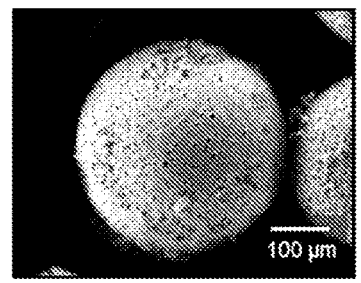
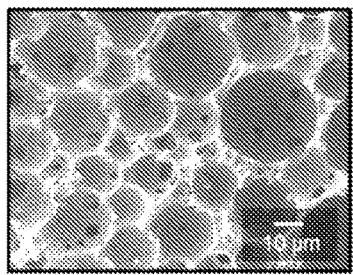 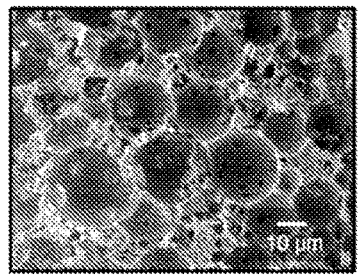 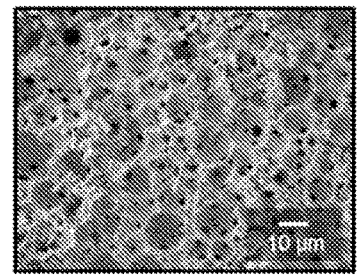
FIG. 9A  FIG. 9B  FIG. 9C

POROUS MICROPARTICLES WITH HIGH LOADING EFFICIENCIES

CROSS-REFERENCE TO RELATED APPLICATION

This application claims the benefit of U.S. Provisional Patent Application No. 61/901,771 filed Nov. 8, 2013, the entirety of which is incorporated herein by reference.

TECHNICAL FIELD

As disclosed herein are porous microparticles and methods of making the porous microparticles, which includes porous microparticles that encapsulate one or more substances that are biocompatible and/or bioactive in nature and may be of use in a biologic system.

BACKGROUND

Introducing biocompatible and/or bioactive substances to a biologic system has its challenges. An ideal delivery would follow zero-order kinetics, such that the blood level after delivery of the biocompatible and/or bioactive substance remains constant. Current delivery systems, including porous polymers have been described but macroporous polymers have never been shown to offer zero-order release. Some porous polymers are strongly adhesive to the gastrointestinal mucus and cellular lining of the body, thereby limiting their use for local delivery to other sites. In addition, macroporous polymers have only been found to exhibit first-order kinetics. Early evidence using polymers of poly (lactide-co-glycolide) suggests that after 12 hours or so, there may be a near zero-order kinetics; however, release of protein was considered low. Using hollow microspheres of poly(lactide-co-glycolide), others have ultrasonically produced holes in the spheres, which, it was suggested may provide a means to releasing substances within its core.

With current microspheres, loading efficiencies of the current systems remains quite low because loading occurs after the polymer particles are formed, hence after they have polymerized.

In addition to the above issues and the low encapsulation efficiency currently found with said systems, there are further limitations with current microspheres that include particle size distribution, solvent removal, and bioactivity loss.

The invention described improves upon current systems and also overcomes challenges just described.

SUMMARY

Described herein are improvements to current polymer delivery systems, providing new polymer compositions that are also capable of encapsulating with very high loading efficiencies one or more desired substances, including biocompatible and/or bioactive substances. The polymer compositions and methods of preparing said polymer compositions are described. Said polymer compositions encapsulate the one or more desired substances (e.g., biocompatible and/or bioactive substances) prior to polymerization. The polymer compositions described herein are compatible for local delivery, irrespective of the location of delivery. The polymer compositions described herein may be controlled for size, shape as well as amount of substance to be released. The methods include a solvent free template process for fabricating particles. The microparticle compositions when formed are, thus, solvent-free. In one or more embodiments, said particles are generally uniform. The particles sizes may be tunable and have, themselves, a desired or tunable pore size for the controlled release of one or more the desired substances.

The compositions described herein are porous, thereby suitable for encapsulation and release of said desired substance or combination of substances of compatible size, exhibiting controlled release performance of said substance.

In one or more embodiments, a polymer composition includes a mixture of two components in the form of a double emulsion. The double emulsion is a water-in-oil-in-water emulsion containing a first component and a second component. Said components form a polyHIPE composition that is porous. Said components form a polyMIPE composition that is porous.

The first component comprises an organic phase (continuous or oil phase) with an internal aqueous phase. Said phases are solvent free. The first component is a first emulsion prepared, in some embodiments, as a high internal phase emulsion (HIPE) when the first component has a water (or water-based, aqueous phase) volume of at least about 70% or about 75% or greater. The organic or continuous phase of the first component will comprise at least a first biodegradable polymeric material and at least one initiating agent which is a cross-linking agent. The at least one initiating agent may be a free-radical oxidizing agent or another suitable initiating agent, such as a thermal initiator, UV initiator or redox initiator, and various combinations thereof. The organic phase of the first component is selected by having a low viscosity, suitable hydrophobicity to allow a first emulsification with the aqueous phase, and does not require any organic solvent for the first emulsification. The aqueous phase of the first component will include at least one chemical that prevents Ostwald ripening. The aqueous phase of the first component is water or a water-based solution and may also contain at least one substance, such as a substance that is biocompatible and/or bioactive in a biologic system. The substance when biocompatible and/or bioactive in a biologic system may be one or more cells, enzymes, growth factors, peptides, proteins, pharmaceutical agents, nanoparticles and the like. The substance may be organic or inorganic or have one or more organic or inorganic linkages. A desired amount of the biocompatible and/or bioactive substance may be provided into each microparticle by the methods described herein.

The second component of the double emulsion is an aqueous phase and may contain, in addition to water, a surfactant, an initiator (cross-linking agent) and/or wetting agent. In some embodiments, there is no surfactant in the second component.

The first biodegradable polymeric material of the first component is stabilized with an emulsifier in the continuous or organic phase. The emulsifier is selected as one lacking hydrogen bond donor sites (donors) in its hydrophilic, polar head region. The emulsifier may be an amphiphilic surfactant having a polar, water-soluble head group attached to a nonpolar, water-insoluble hydrocarbon chain. In one or more embodiments, the emulsifier has a hydrophilic-lipophilic balance (HLB) in a range of between about 2 and about 9. In some embodiments, the emulsifier has a hydrophilic-lipophilic balance (HLB) in a range of between about 3 and about 5.

The first biodegradable polymeric material will include: (a) a macromonomer (macromer) having at least one reactive end group, which is biodegradable, and having a suitable viscosity for emulsion in water; and (b) reaction thermodynamics that allow polymerization and/or curing at a physiologic condition. The at least one reactive end group will crosslink the macromer at a thermal or ambient or a physiologic temperature. The molecular weight of the first biodegradable polymeric material will assist in maintaining a viscosity, and preferably a controlled viscosity that replaces (and no longer requiring) a toxic diluent for emulsion stabilization. The at least one reactive end group has at least one unsaturated (double) bond for undergoing free radical cross linking. In one or more embodiments, the at least one reactive end group may be an acrylate end group or a methacrylate end group.

The macromer for the first biodegradable polymeric material will have a selected viscosity and hydrophobicity. In one or more embodiments, the hydrophobicity, determined by an octanol-water partition coefficient (Log P), is greater than 2. In some embodiments, the Log P is in a range of between 2 and 8. In some embodiments, the Log P is in a range of between 2 and 4. The macromer preferably is but is not required to have a viscosity in a range that is near that of water, which is 1 cP. In some embodiments, the viscosity is in a range of between about 0.08 cP and about 1000 cP. In some embodiments, the viscosity is not greater than 150 cP.

Suitable macromers are ones prepared from an ester based monomer or from an anhydride based monomer. A suitable macromer is represented by but is not limited to a biodegradable macromer having one or more ester linkages or a biodegradable macromer having one or more anhydride linkages. Exemplary embodiments include a biodegradable fumarate based monomer having one or more ester linkages (e.g., propylene fumarate dimethacrylate [PFDMA]), a biodegradable diglycol based monomer having one or more ester linkages (e.g., ethylene glycol dimethacrylate [EGDMA]), a butane diol dimethacrylate [BDMA]) and a biodegradable acrylic based monomer having one or more anhydride linkages (e.g., methacrylic anhydride [MA]).

The first component of the high internal phase emulsion or the medium internal phase emulsion is formed by mechanical dispersion of the above described constituents. The first component is formed after a first emulsification in a solvent free system.

The double emulsion includes introducing the first component into the second component. The first component is introduced drop wise, as droplets, into the second component, thereby forming a second emulsion, which is essentially a water-in-oil-in-water emulsion. The second component is solvent free. The second emulsion will comprise porous microparticle compositions. Each microparticle composition includes the first component, in which the aqueous phase of the first component become encapsulated in a polymeric matrix (organic matrix). When the first component contains the at least one additional substance (which may or may not be bioactive and/or may or may not be biocompatible), then the microparticle compositions when formed will retain the at least one substance in the aqueous phase of the first component, thereby encapsulating the at least one substance within the polymeric matrix. The microparticle compositions may be spherical or somewhat spherical in shape, and may be so shaped as desired by means described herein. Said means include controlling the size and shape of the droplets, controlling the rate of droplet introduction (into the second component), and controlling the rate of injection and/or volume of injection of the first component into the second component. Microparticle composition will, in one or more embodiments, be capable of having a well-defined size and/or shape, said well-defined size and/or shape provided by the rate of droplet introduction (into the second component), the rate of injection and/or the volume of injection of the first component into the second component. In one or more embodiments, microparticle compositions will have a cross sectional diameter (in at least one direction) that is from about 20 micrometers to about 1000 micrometers. Microparticle compositions will, in other embodiments, have a cross sectional diameter (in at least one direction) that is from about 20 micrometers to about 100 micrometers. Further, microparticle compositions will, in other embodiments, have a cross sectional diameter (in at least one direction) that is from about 100 micrometers to about 500 micrometers. In other embodiments, microparticle compositions will have a cross sectional diameter (in at least one direction) that is from about 150 micrometers to about 800 micrometers, or from about 200 micrometers to about 800 micrometers. In additional embodiments, microparticle compositions will have a cross sectional diameter (in at least one direction) that is from about 300 micrometers to about 1000 micrometers. A standard deviation of the microparticle compositions is generally not more than 50 micrometers when the cross-sectional diameter is greater than 300 micrometers. The standard deviation may be less than 40 micrometers, or less than 35 micrometers, or less than 30 micrometers, or less than 25 micrometers. The standard deviation of the microparticle compositions may be between about 20 micrometers and 35 micrometers when the cross-sectional diameter is greater than 300 micrometers.

When fully polymerized and hardened, the compositions form porous microparticles. Hardening may be performed at a predetermined time or when desired after performing the second emulsification. Hardening includes initiating cross-linking after droplets are introduced into the second component, such as by a thermal means, a light means, a redox means, or other suitable means, depending on the type of initiator incorporated into the first component. Cross-linking and hardening of the microparticle compositions maintains the porous microparticles in their initially formed shape, unless further shaping occurs prior to completion of polymerization. Cross-linking and hardening of the microparticle compositions may occur while the compositions remain in the second component. Cross-linking and hardening of the microparticle compositions may occur when the microparticle composition is in another environment removed from or transitioning from the second component.

Cross-linking and, thus, hardening provides porous microparticles with a three dimensional structural matrix and porous region that includes a plurality of pores or spaces therein. Porous microparticles may be dried in air or under vacuum to remove water after cross-linking. Porous microparticles may be dried by freeze drying. Alternative means known in the art are also acceptable for drying said particles. Porous microparticles may be stored for later use after cross-linking. In one or more embodiments, porous microparticles are fully hardened before being introduced into a biologic system. In additional embodiments, porous microparticles may be fully hardened after they are introduced into a biologic system. No further manipulation of the porous microparticles is required after they are fully polymerized, especially when porous microparticles are polymerized in an aqueous phase or in biocompatible fluid, such as one that is biocompatible with or is similar or the same as a biologic system. Porous microparticles, when formed from a composition in which the first component contains the at least one substance (e.g., biocompatible and/or bioactive substance), do not require further seeding or implantation with the substance or in a biologic fluid after being formed. The porous microparticles when formed do not need to undergo solvent evaporation, since no solvent is required for formation. The porous microparticles described herein do not need to be further washed or immersed in a solvent to dissolve/remove certain undesirable components. This is because the porous microparticles described herein are formed of components that are compatible with a biologic system. It is also understood that said porous microparticles may be used in other systems, such as engineering, chemical, and/or environmental systems that may or may not include biologic material(s). It is understood that said porous microparticles may be loaded and, hence, encapsulated with a substance useful in a system other than biologic system, such as a physical, chemical and/or environmental systems that may or may not include biologic material(s).

In one or more embodiments, a microparticle composition is described that includes a polymeric matrix and a porous region, said microparticle composition having been derived from a double emulsion preparation. Generally, the polymeric matrix is shaped and sized as a microparticle. The polymeric matrix will often present as a generally spherical or somewhat spherical shape. The porous region includes an interconnected network of pores that reside within the polymeric matrix. The polymeric matrix may also present as an ovoid or non-spherical shape. The polymeric matrix will include at least the first biodegradable polymeric material and the at least one initiating agent, which is a cross-linking agent, as well as any other constituent of the organic phase of the first component. The polymeric matrix when hardened will form the three dimensional structural matrix of the formed porous microparticle.

A plurality of the pores in the porous region may be interconnected, thereby providing an internal microarchitecture. Not all pores are interconnected. When porous microparticles are formed from a composition that includes the at least one substance, the at least one substance will reside within the porous region. In one or more forms, many of the pores will include therein the at least one substance. In some embodiments, the pores are relatively uniform. In some embodiments, the substance is entrapped in the internal architecture of the microparticle composition. In some embodiments, the substance will reside along the pore wall. In some embodiments, the substance is adsorbed to the pore wall. The porous region will further comprise other constituents of the aqueous phase of the first component, unless said constituents did not adsorb or diffused prior to introduction of the microparticles to a system. Said constituents may be releasable upon degradation of the polymeric matrix in the system.

In the porous region of a microparticle composition, an individual pore will have a size that ranges from about 1 micrometer to about 100 micrometers. In some embodiments, the pore size will range from about 1 micrometer to about 50 micrometers, and/or from about 2 micrometers to about 40 micrometers, and/or from about 5 micrometers to about 35 micrometers, and/or from about 10 micrometers to about 30 micrometers, and/or from about 5 micrometers to about 20 micrometers. In some embodiments, the pores are relatively uniform.

A method of making the microparticle compositions described herein includes a first mixing or emulsification of the organic phase and the aqueous phase to form a first emulsion, which may be a high internal phase emulsion. The first mixing may also form a medium internal phase emulsion. After the first emulsification, which forms the first emulsion (or the high internal phase emulsion; or the medium internal phase emulsion), the first emulsion is introduced as droplets into the second component, forming a second emulsion. The second emulsion will comprise a plurality of microparticle compositions. The number of microparticle compositions generally correspond with the number of droplets introduced into the second component. Hardening of the microparticle compositions occur via cross-linking, which provides hardened porous microparticles having a three dimensional hardened structural matrix with a porous region therein comprising pores or spaces, in which a plurality of the pores or spaces are interconnected. Hardening is initiated by any means for initiating cross-linking, said means will be compatible with the initiating agent contained in the organic phase. No further processing steps are required. Thus, the method described herein does not require additional seeding or implantation with a substance, such as a biocompatible and/or bioactive substance, when the microparticle compositions are prepared with at least one biocompatible and/or bioactive contained in the organic phase. The method does not require pre-casting of the compositions in a mold. The method does not require any additional evaporation of a solvent. The method does not require additional washing or immersion of the porous microparticles after hardening for removal of undesirable and potentially toxic components.

Microparticle compositions and porous microparticles may be introduced to a system (e.g., biologic system) by any suitable means. For a biologic system, said means of introducing include oral, parenteral, intramuscular, intravenous, by injection, by inhalant, and the like. Microparticle compositions may be delivered locally, and in situ. Microparticle compositions and porous microparticles may also be delivered cooperatively with other means for delivery or into another three-dimensional network prior to delivery. Microparticle compositions and porous microparticles described herein are also suitable for any other applications for which the porous microparticles may be useful or desired, whether or not the porous microparticles encapsulate at least one substance, such as a biocompatible and/or bioactive substance.

In one or more embodiments is a double emulsion comprising a first component comprising an organic phase. The organic phase includes at least a biodegradable polymeric material. The biodegradable polymeric material comprises at least one end group selected from an acrylate and a methacrylate and one or more linkages selected from an anhydride and an ester. The biodegradable polymeric material may be a monomer. The biodegradable polymeric material generally has an octanol-water partition coefficient of between about 2 and about 8. The biodegradable polymeric material generally has a viscosity of between about 0.08 cP and about 1000 cP. The viscosity may be at or less than 150 cP. The biodegradable polymeric material is stabilized with a quantity of an emulsifier lacking hydrogen bond donors in its hydrophilic head region while having a hydrophilic-lipophilic balance in a range of between about 2 and about 9. The organic phase further comprises at least one cross-linking agent. The first component further includes an aqueous phase. The aqueous phase may also contain a chemical to prevent Ostwald ripening. In some embodiments, the first component forms a high internal phase emulsion. In some embodiments, the first component forms a medium internal phase emulsion. The double emulsion further comprises a second component. The second component is a second aqueous phase. The octanol-water partition coefficient of the biodegradable polymeric material is between about 2 and about 4. The first component further comprises one or more of a surfactant and a wetting agent. The chemical to prevent Ostwald ripening is a salt. The cross-linking agent is a non aqueous free-radical oxidizing agent, a thermal initiator, UV initiator, a redox initiator, and various combinations thereof. The hydrophilic-lipophilic balance of the emulsifier is in a range of between about 3 and about 5. The aqueous phase further comprises a substance selected to be one or more of compatible with and active in a biologic system. The first component is a medium internal phase emulsion.

Also described herein is a method of making a double emulsion comprising: preparing by mechanical dispersion a first component as a high internal phase emulsion or a medium phase internal emulsion comprising at least one biodegradable polymeric material and at least one cross-linking agent in an organic phase and a chemical to prevent Ostwald ripening in an aqueous phase; adding drop wise the first component in a second component to form a porous microparticle composition, wherein the aqueous phase of the first component is encapsulated in the porous microparticle composition. The first component further comprises a substance selected to be one or more of compatible with and active in a biologic system in the aqueous phase. The second component is an aqueous phase having a fluid velocity. The method further comprises initiating crosslinking. The initiating crosslinking occurs after adding drop wise the first component in the second component. The diameter of the porous microparticle is affected by any one or more of the group consisting of a rate of adding drop wise the first component in the second component, viscosity of the first component, a velocity of the second component, a diameter of a passage for adding drop wise the first component, and characteristics of a path containing the second component. The method of claim 10, wherein the aqueous phase of the first component is encapsulated in the porous microparticle compositions prior to polymerization.

Further described is a method of making a composition comprising combining by mechanical dispersion a high internal phase emulsion or a medium phase internal emulsion, the emulsion containing a cross-linking initiator in the continuous phase and a first aqueous phase. A substance, such as one selected to be one or more of compatible with and active in a biologic system, may be in the first aqueous phase. A crosslinking agent may be in the aqueous phase. The method includes adding drop wise the high internal phase emulsion or the medium internal phase emulsion into a second aqueous phase solution. After adding the high internal phase emulsion or the medium internal phase emulsion into the second aqueous phase solution, the first component is encapsulated in the continuous phase, such that the continuous phase has a shape of a microsphere. The rate of adding has an effect on the average size of the microsphere. The velocity of the aqueous phase when adding the high internal phase emulsion (or the medium internal phase emulsion) into the second aqueous phase solution has an effect on the average size of the microsphere.

Still further is described a composition comprising a structural matrix and a porous region. The structural matrix comprises a biodegradable polymeric material. The biodegradable polymeric material comprises at least one end group selected from an acrylate and a methacrylate, and one or more linkages selected from an anhydride and an ester. The biodegradable polymeric material may be a monomer. The biodegradable polymeric material has an octanol-water partition coefficient of between about 2 and about 8. The biodegradable polymeric material has a viscosity of between about 0.08 cP and about 1000 cP. The biodegradable polymeric material is stabilized with a quantity of an emulsifier lacking hydrogen bond donors in its hydrophilic head region while having a hydrophilic-lipophilic balance in a range of between about 2 and about 9. The structural matrix further comprises a cross-linking agent. The porous region contains at least one substance selected to be one or more of compatible with and active in a biologic system. The structural matrix further comprises an emulsifier. The composition may have a shape that is spherical and a cross sectional diameter that is of a generally uniform size, ranging from 20 micrometers to about 1000, with a standard deviation that is not more than 50 nm when the cross-sectional diameter is greater than 300 micrometers. The structural matrix may be formed from a high internal phase emulsion in which the biodegradable polymeric material has a viscosity that is about or less than about 150 cP. The structural matrix may be formed from a medium internal phase emulsion in which the biodegradable polymeric material has a viscosity that is about or less than about 150 cP. The composition is biodegradable when in the biologic system, releasing the at least one substance into the biologic system.

These and other details relating to the various embodiments are further described in the descriptions below.

BRIEF DESCRIPTION OF THE DRAWINGS

Various embodiments will be explained in more detail with reference to the drawings in which:

FIG. 2 depicts a general structure of a propylene fumarate dimethacrylate macromer;

FIG. 3 depicts a general structure of an ethylene glycol dimethacrylate macromer;

FIG. 4 depicts general structure of a butane diol dimethacrylate macromer;

FIG. 5 depicts general structure of a methacrylate anhydride macromer;

FIGS. 6A-6D depict representative porous microparticles described herein of different cross-sectional diameters, including ~800 micrometers (FIG. 6A), ~670 micrometers (FIG. 6B), ~570 micrometers (FIG. 6C), ~400 micrometers (FIG. 6D), and ~230 micrometers (FIG. 6E);

FIG. 7 illustrates a representative relationship between velocity and particle size (cross sectional diameter);

FIGS. 8A-8C illustrates representative porous microparticles having differing pore sizes;

FIGS. 9A-9C show in close up the pores of the porous microparticles of FIGS. 8A-8C, respectively.

DESCRIPTION

Figure 1A:
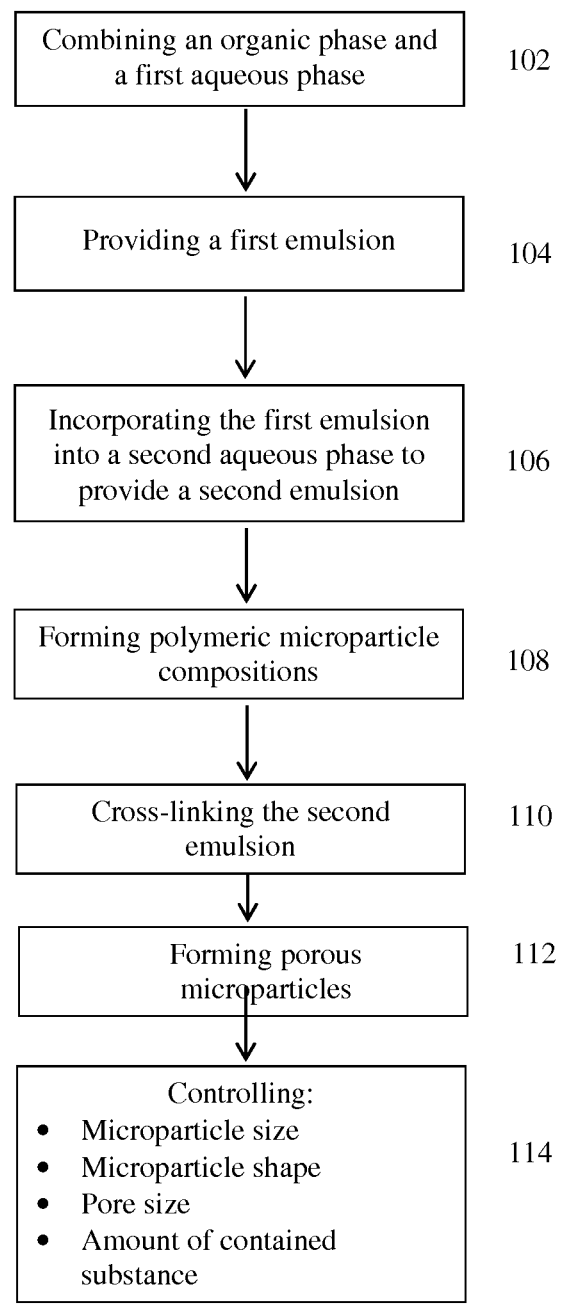
FIG. 1A depicts a representative method of preparing polymeric microparticle compositions described herein.

Although making and using various embodiments are discussed in detail below, it should be appreciated that as described herein are provided many inventive concepts that may be embodied in a wide variety of contexts. Embodiments discussed herein are merely representative and do not limit the scope of the invention.

An improved polymer delivery system is described which provides polymeric microparticle compositions and porous microparticles formed therefrom. In some embodiments, both the polymeric microparticle compositions and porous microparticles encapsulate at least one substance. The encapsulation occurs prior to polymerization. The amount of the at least one substance that may be encapsulated is controlled by the methods described herein. In one or more embodiments, the polymeric microparticle compositions and porous microparticles are loaded with a high amount of the at least one substance. In other embodiments, the polymeric microparticle compositions and porous microparticles are loaded with a lesser amount of the at least one substance. In one or more embodiments, the substance is one that is compatible with and/or active in a biologic system. Said substances are generally water compatible substances, including but not limited to as cells, enzymes, growth factors, peptides, proteins, pharmaceutical agents, co-factors, fatty acids, nanoparticles and the like. Said substances only need be of a size that will be incorporated in the polymeric microparticle compositions and thereby encapsulated in the porous microparticles as described further below. A substance may also have a modifier, such as one that enables the substance to behave in a biologic or physiologic manner. The modifier is typically small (about 5-200 nanometers or less than 1000 nm or some size therein) and often includes a hydrophobic component or moiety. An example of a modifier is but is not limited to an inorganic nanoparticle. The inorganic nanoparticle may be further linked to a hydrophobic component or fatty acid. Another example of a modifier is but is not limited to an amphiphilic molecule having a cell-adhesion or adhesive-like moiety (e.g., fatty acid conjugated to cell-adhesion molecule, peptide or protein).

It is understood that with the methods described herein, other substances may also be incorporated alone or in combination.

The polymeric microparticle compositions and porous microparticles are prepared as a first emulsion followed by the formation of a second emulsion. The first emulsion is, in some embodiments, a high internal phase emulsion (HIPE). This first emulsion provides a first component, which is a water-in-oil emulsion having an internal phase volume fraction that is aqueous (water or water-based) with or without the substance therein, such that the aqueous phase volume fraction makes up about 74% or up to 99% of the total emulsion volume, hence a 74% to 99% droplet phase. The first emulsion is, in some embodiments, a medium internal phase emulsion (MIPE). This first emulsion forms a first component, which is a water-in-oil emulsion having an internal phase volume fraction that is aqueous (water or water-based) with or without the substance therein, such that the aqueous phase volume fraction makes up about 40% or up to about 74% of the total emulsion volume, hence a 40% to 74% droplet phase. In some embodiments, the aqueous phase volume fraction makes up greater than 50% or up to about 99% of the total emulsion volume (greater than 50% to 99% droplet phase). In some embodiments, the aqueous phase volume fraction makes up greater than 60% or up to about 99% of the total emulsion volume (greater than 60% to 99% droplet phase). In some embodiments, the aqueous phase volume fraction makes up greater than 70% or up to about 99% of the total emulsion volume (greater than 70% to 99% droplet phase). It is understood that in some embodiments the first component may include an internal phase volume that may be as low as 30%. The organic or continuous phase of the first component includes at least one stabilized biodegradable polymeric material (e.g., macromers as will be further described below) that is functionalized and capable of undergoing further polymerization.

Fabrication of HIPEs have been described in U.S. patent application Ser. No. 13/651,362 (the entirety of which is incorporated herein by reference). Said HIPEs (as well as MIPEs) have now been improved upon that are also useful in preparing a double emulsion, as described herein. Said double emulsion provides a polymeric microparticle composition capable of encapsulating a substance. The polymeric microparticle compositions when fully formed and hardened provide improved porous microparticles. As further described herein are means for controlling one or more of the following as it relates to the polymeric microparticle compositions and/or porous microparticles: particle size, particle shape, pore size, and the amount of substance to be loaded. The polymer chemistry chosen for the first component may be further tuned to alter and manipulate structural hardness (e.g., compressive strength) of the final formed porous microparticle. Fabrication of MIPEs are similarly performed, in which the water content is adjusted as described above.

The first component as described herein is biodegradable, prepared with a biodegradable polymeric material in the organic phase. The biodegradable polymeric material comprises a functionalized macromer capable of undergoing further polymerization. In some embodiments, the first component comprises only a single macromer. The first component does not include oligomers or polymers. When forming a HIPE, the amount of macromer in the first component will range from about 1 wt. % to 25 wt. %. When formed as a MIPE, the amount of macromer in the first component will range from about 26 wt. % to 60 wt. %. The macromer is provided as the cross-linkable component. No other cross-linkable component (e.g., monomer, or otherwise) is required.

The macromer used in the first component described herein is either an ester based monomer or an anhydride based monomer and will have at least one reactive end group, which is biodegradable, a suitable hydrophobicity (determined by an octanol-water partition coefficient [Log P]) and viscosity for emulsion in water, and may be polymerized and/or cured at or near physiologic conditions. In some embodiments, the macromer itself may be prepared via a two-step reaction, such as that described in U.S. patent application Ser. No. 13/651,362, which includes: (i) backbone synthesis, and (ii) functionalization. In some embodiments, the macromer is considered a monomer. Prior to polymerization, the first component does not comprise a polymer. Thus, the macromer is not dissolved in a polymer. The macromer is also not dissolved in a diluent.

The at least one reactive end group of the macromer described herein is one that crosslinks at a thermal temperature or a lower temperature (e.g., ambient temperature, physiologic temperature) and of a low molecular weight that maintains a low viscosity for the macromer, hence acting to replace and no longer requiring addition of a toxic diluent. The at least one reactive end group has at least one unsaturated (double) bond for undergoing free radical cross linking. The carbon-carbon double bond in the at least one reactive end group allows thermal decomposition to occur in the presence of the initiators, to be described further. The initiator or cross-linking agent suitable for cross-linking is one that undergoes free radical cross-linking. In one or more embodiments, the at least one reactive end group generally includes an acrylate end group or a methacrylate end group.

The hydrophobicity of the macromer described herein is defined by a Log P at about or greater than 2. It may also be defined by a Log P from between about 2 and about 8. It may also be defined by a Log P from between about 2 and about 4. A host of suitable macromers may be identified using available tools, including online services, such as one provided by Molinspiration Cheminformatics. For example, Molinspiration Cheminformatics provides model predictions of the Log P for more than 12,000 molecules or compounds, generally calculated from the sum of non-overlapping molecular fragments after fitting calculated Log P with experimental Log P values.

TABLE 1

Estimated octanol-water partition coefficients

| Molecule | LogP |
| --- | --- |
| styrene | 2.8 |
| divinyl benzene | 3.6 |
| PFDA | 2.3 |
| PFDMA | 3.4 |
| BDMA | 3.0 |
| EGDMA | 2.2 |
| MA | 2.4 |

The Log P value of various representative compounds suitable under the definition provided herein are provided in TABLE 1, including PFDMA, which is propylene fumarate dimethacrylate (as depicted in FIG. 2); BDMA, which is butane diol dimethacrylate (as depicted in FIG. 4); EGDMA, which is ethylene glycol dimethacrylate (as depicted in FIG. 3); and MA, which is methacrylic anhydride (as depicted in FIG. 5). These suitable and representative macromers are compared to ones that are already used by alternative methods to prepare a stable HIPE or a stable MIPE, such as styrene and divinyl benzene.

The viscosity of the macromer described herein is defined as being in a range between about 0.08 cP and about 1000 cP. In some embodiments, the viscosity is near that of water, which is 1 cP. Generally, the viscosity is not greater than 150 cP.

The macromer as described herein may also be characterized as a biodegradable polymeric material having one or more ester linkages or a biodegradable polymeric material having one or more anhydride linkages. Exemplary embodiments include but are not limited to a biodegradable fumarate based macromer having one or more ester linkages (e.g., propylene fumarate dimethacrylate [PFDMA]), a biodegradable glycol based macromer having one or more ester linkages (e.g., ethylene glycol dimethacrylate [EGDMA]), a hydroxy (e.g., diol) based macromer having one or more ester linkages (e.g., butane diol dimethacrylate [BDMA]) and a biodegradable acrylic based macromer having one or more anhydride linkages (e.g., methacrylic anhydride [MA]).

The macromer in the first component described herein is stabilized in the continuous phase by an emulsifier. The emulsifier may be an amphiphilic surfactant having a polar, water-soluble head group attached to a nonpolar, water-insoluble hydrocarbon chain. The emulsifier is selected as one lacking hydrogen bond donor sites (donors) in its hydrophilic, polar head region. The emulsifier has, in one or more embodiments, a hydrophilic-lipophilic balance (HLB) in a range of between about 2 and about 9. In some embodiments, the emulsifier has a hydrophilic-lipophilic balance (HLB) in a range of between about 3 and about 5.

In the embodiments described, the prepared first component is a water-in-oil emulsion comprising a stabilized biodegradable polymeric material and at least one initiating agent or cross-linking agent in its continuous (oil or organic) phase. The stabilizer is the emulsifier, in an amount generally between about 5 wt. % and about 20 wt. % or may be greater than about 30 wt. % (based on the total weight in the organic phase). The cross-linking agent may be any initiator capable of initiating polymeric cross-linking by a thermal reaction, by light, by a redox reaction, or by an oxidizing reaction (e.g., thermal initiator, light sensitive initiator, redox initiator, free radical initiator, free-radical oxidizing initiator). In one or more embodiments, the cross-linking agent or initiator is organically soluble. In one or more embodiments, the cross-linking agent is a photoactivatable initiator or photoinitiator, activatable, for example, by actinic radiation. The quantity of the cross-linking agent is in an amount that is sufficient to initiate extensive cross-linking of a macromer chain (of unsaturated double bonds of the one or more end groups). The amount of cross-linking agent is generally up to about 5 wt. % or may be up to or about 2 wt. % (based on the total weight in the organic phase). The amount of the cross-linking agent may be adjusted to effect the rate or time to harden (fully polymerize). As described herein, unlike alternative HIPEs or MIPEs, there is no solvent or diluent or paraffin material in the continuous phase (in the first component prior to polymerization). Similarly, there is no solvent, diluent or paraffin material in the second component.

The first component further comprises an aqueous phase that is water or water-based, having one or more additives. One of the one or more additives is often a chemical preventing Ostwald ripening. The at least one chemical that prevents Ostwald ripening may be a salt or an electrolyte. Only a small amount of the chemical preventing Ostwald ripening is typically required, generally about 1 to about 5% (v/v). The additive may further comprise a modifier. In some embodiments, the aqueous phase may further comprise a second initiating agent. This has been found to be useful when desiring to alter pore size of the formed porous microparticle.

The first component is prepared as illustrated in FIG. 1A, box 102 and 104, such that in the first emulsion the at least one stabilized macromer and the cross-linking agent are in the continuous (organic) phase and the chemical preventing Ostwald ripening as well as the at least one bioactive and/or biocompatible substance, when included, is in the dispersed (aqueous) phase. In some embodiments, as described above, a cross-linking agent may also be included in the aqueous phase.

In some embodiments, the macromer is initially stabilized with the emulsifier, after which the initiating agent is added. To prevent early polymerization or cross-linking, the initiating agent should be one that must be activated to initiate cross-linking. The ratio of the organic phase to the aqueous phase can be used to obtain a desired porosity of the final porous microparticle. In addition, the final porous microparticle may be formulated by modifying mixing speed and/or the amount of emulsifier used to stabilize the macromer. Such modifications are used to specify pore size and/or pore architecture.

Figures 1B, 1C:
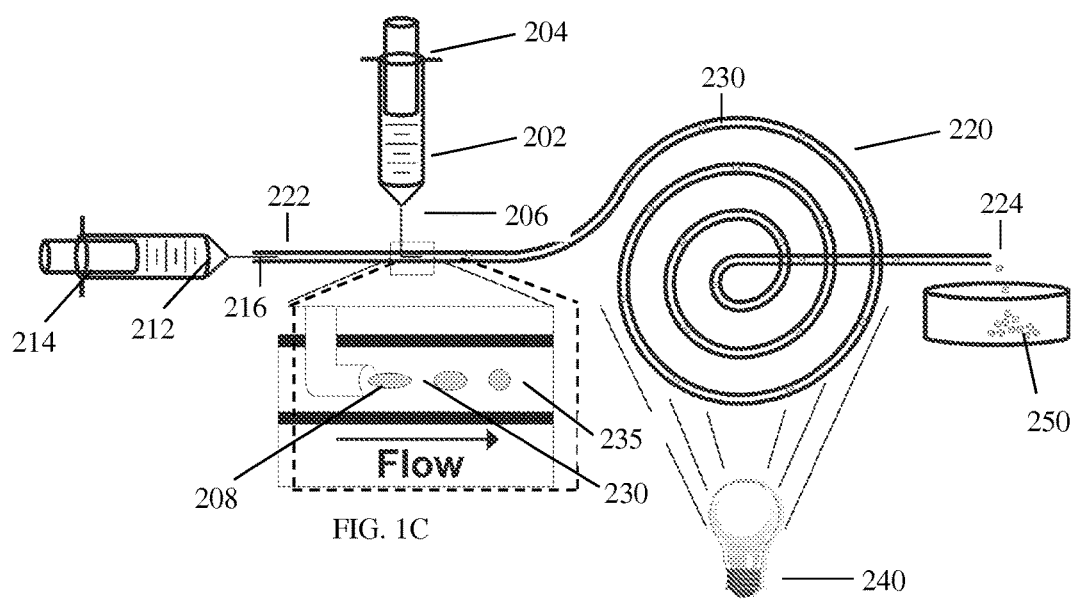
FIG. 1B depicts a representative schematic of a fabrication process and system described herein.
FIG. 1C depicts an enlarged view of the boxed region along tubing 220 of FIG. 1B.

The first component is then incorporated drop wise into the second component, as depicted in FIG. 1A, box 106, and FIGS. 1B and 1C. The second component typically includes an (water-rich) phase and a small amount (generally about 3 wt. % or up to about 3 wt. % of the second component) of at least one second stabilizing agent, which may include a combination of several stabilizing agents, such as polyvinyl alcohol, Tween 80, and Tween 20. Said one or more stabilizing agents should be those that increases external phase viscosity and acts to decrease interfacial tension at the surface of the shaped object. Said stabilizing may also be one that reduces droplet coalescence. Polymeric microparticle shaped compositions form with drop wise addition of the first component (box 108, FIG. 1A). Variables that may be modified, which directly affect the formation of the polymeric microparticle compositions, include stir rate when adding droplets, injection (flow) rate of the droplets, and volume of each droplet. Cross-linking is initiated, as depicted in FIG. 1A, box 110, by activating the initiating agent, present at least in the organic phase of the first component. With cross-linking, porous microparticles are formed and when fully hardened include a structural matrix encapsulating pores. Thus, in one or more embodiments, cross-linking only occurs after droplet formation and exposure to a condition that activates the initiating agent. When the aqueous phase of the first component includes a substance that is biocompatible with or is an active agent, the fully hardened porous microparticles encapsulate the substance therein. The pores of the porous microparticles may be controlled by selecting a specific flow rate of the first component (droplets) and/or flow velocity of the second component. For example, the rate of flow (injection) of droplets may be adjusted from between about 0.1 to about 3 mL/hour, as examples. In addition, the flow velocity (stir rate) of the second component may be adjusted from between about 1 to about 500 cm/min. These adjustments created monodisperse porous microparticles having average particle sizes that were in a range from between about 100 micrometers to about 1000 micrometers (FIG. 7). Other ranges are also expected with faster or slower flow rates, faster or slower flow velocities, and/or larger or smaller droplets.

A representative system for fabricating porous microspheres as described herein is depicted schematically in FIG. 1B, in which the first component 202 (comprising a described HIPE composition or a described MIPE composition) is loaded into first device 204, depicted in the figure as a pump or syringe. First composition 202 is optionally passed through a fluid passage 206, depicted in the figure as a needle, and released (e.g., drop wise) through a specifically sized outlet 208. Outlet 208 feeds first component 202 with second component 212, which is flowing through tubing 220 as it exits second device 214, depicted as a pump or syringe having a fluid passage 216 positioned in parallel with tubing 220. Fluid movement is generally continuous and in the direction depicted by the arrow in FIG. 1C. As is also shown in FIG. 1C, the outlet 208 is configured in such a way to release first component 202 in a flow pattern that is generally parallel to the flow path or direction of second component 212 in tubing 220. The direction and size of outlet 208 also assists in providing the cross-sectional diameter of shaped objects 230 as they exit outlet 208. Shaped objects 230 may exit as a first shape and then may naturally form and revert to a more stable shape, which is often a more spherical shape 235 when the viscosity of the first component has a lower viscosity. A shaped object 230 may be more oblong and remain as such when the viscosity of the first component (as directed by viscosity of the biodegradable polymeric material) has a higher viscosity. Tubing 220 will generally provide a directional movement or flow from a first end 222 to a second end 224 (FIG. 1B). A portion of said tubing 220 will pass an excitation or initiation region which induces polymerization. Polymerization may be induced by device 240 (e.g., light and/or heat, depicted in FIG. 1B as a light source, or a UV irradiation lamp) or other means for inducing polymerization. With polymerization, said spherical shaped objects 235 will cure to form hardened porous microspheres 250, which are collected at second end 224. Porous microspheres 250 may undergo further processing and/or filtering prior to use. Scaling of such a system is possible to incorporate cells and/or other biologic substances directly into the porous microparticles.

FIGS. 6A-6D illustrates porous microparticles formed with sizes ranging from about 800 micrometers (FIG. 6A) to about 230 micrometers (FIG. 6E).

In some examples, a first component was prepared, generally as described above using a speed mixer. A stabilizing EGDMA was mixed with several differing amounts of surfactant (polyglycerol polyricinoleate (PGPR)), 10 wt. %, 20 wt. %, or 30 wt. % (based on the weight of the macromer). In addition, an organic phase, organically soluble, free radical photoinitiator, 2,2-dimethoxy-2-phenylacetophenone (DMPA), in an amount of 2 wt. %, was added to each mix (also prior to emulsification). Once mixed, an aqueous solution containing calcium chloride (1% v/v) in deionized water was added to each organic phase (~75% v). Addition of the calcium chloride generally occurred in the three additions, each of which involved blending in a dual asymmetric centrifugal mixer (e.g., FlackTek Speedmixer DAC 10 FVZ-K). The speed here was about 500 rpm for 2.5 minutes. While, this preparation included an organic phase soluble free radical initiator, an aqueous phase initiator could also have been added, either as an alternative or as in addition. The calcium chloride was added as the electrolyte for preventing Ostwald ripening.

After blending, a first emulsion was formed, which was transferred to a system as described above for fabricating microspheres. In this example, a syringe that was protected from light and stored at 8° C. until ready for use was loaded with the first emulsion. A needle was used as the fluid passage to introduce the first emulsion into the second component. Addition of the first emulsion was drop wise (e.g., via an infusion pump) into the second component, which was an aqueous phase comprising 3 wt. % poly(vinyl) alcohol moving through a plastic (relatively transparent) tubing made of Tygon® (last registered to Saint-Gobain Performance Plastics Corporation, Ohio, USA). Cross-linking was initiated by exposing a portion of the tubing to ultraviolet light. In this instance, a transilluminator illuminating at 365 nm was used for a duration of about 2.5 minutes, such that the drop wise emulsion composition exiting the syringe was thereafter in the presence of the transilluminator for about 2.5 minutes. The photocuring allowed the cross-linking to occur within minutes at room temperature. Photocuring also eliminated the need for purification. Porous microspheres were then formed and collected. The collected microspheres were filtered using vacuum aspiration and dried in vacuo for about 24 hours; some were dried for more than 24 hours. Average particle size (diameter) and average pore size (diameter) were measured using a scanning electron microscope (SEM). SEM analysis was performed also helped evaluate overall morphology of the porous microspheres. At least 10 particles were imaged to obtain particle size and at least 50 pores were analyzed to obtain average pore size. In one example, with a 30 gauge needle, a 1.6 mm inner diameter tubing, and injection of the first component at a rate of 0.2 ml/hour, particles were greater than 300 micrometers. When the same gauge needle with 0.8 mm tubing was used and injection rate of the first component was 6.0 mL/min, porous microparticles had an average diameter of less than 300 micrometers, and generally between 200 micrometers and 300 micrometers.

Variations in needle diameter, tubing diameter, aqueous flow rate, and emulsion ejection rate were modulated in order to create desired particle sizes. For example, decreasing needle diameter decreased droplet and particle size.

Additionally, changing the tubing inner diameter in conjunction with some above variables was found to influence particle size. For instance, a 0.8 mm tubing yielded the smallest porous microparticles and a 1.6 mm tubing provided the largest porous microparticles. In other trials, the largest porous microparticles were fabricated using 1.6 mm tubing, a 27 gauge needle, and an external velocity of the second component that was 14.9 cm/min. The smallest porous microparticles were created using 0.8 mm tubing, a 30 gauge needle, and an external velocity of the second component that was 298.4 cm/min.

Continuous phase flow velocity (of the second component) and droplet phase viscosity (of the first component) are two important factors contributing to droplet size, shape and uniformity. The fluid velocity relates to the shear force on the shaped object that is released from the outlet into the second component (FIG. 1C). The viscosity of the droplet (pre cure viscosity) also effected with particle size and shape. The pre-cure viscosity (the viscosity prior to polymerization) described herein is suitable for injection. With EGDMA, which has a relatively low viscosity, the porous microspheres when formed were generally uniform and spherical. On the other hand, with a higher viscosity HIPE or MIPE emulsion, the shape of the object when ejected may be more oblong. Similarly, when the ejection rate of the emulsion into the second component is high, the droplet is "jetted" from the needle, forming small and variable size droplets. These relationships generally hold true when the Reynolds number is <<1, indicating laminar flow, and explains why smaller tubing when used allowed particle diameters to be below 500 micrometers.

Aqueous flow velocity of the second component also effected particle size as can be seen in FIG. 7. Using a same tubing diameter (1.6 mm) and adjusting the flow rate from 1.2 mL/min, to 3.0 mL/min, to 4.0 mL/min, to 5.0 mL/min (which increased velocity from 15 cm/min, to 37 cm/min, to 50 cm/min, to 62 cm/min) was found to decrease average particle diameter from 814 micrometers to 418 micrometers. Lower tubing sizes allowed even higher flow velocities, which, then, provided particles with diameters that were less than 300 micrometers. Particles having an average diameter of about 229 micrometers were obtained when the external flow rate was 6.0 ml/min (flow velocity of 298 cm/min) and the injection rate of the emulsion into the second component was up to about 1.0 mL/hr. Generally, the particles when formed were relatively uniform, such that the standard deviation was only between about 25-35 micrometers.

Figure 10:
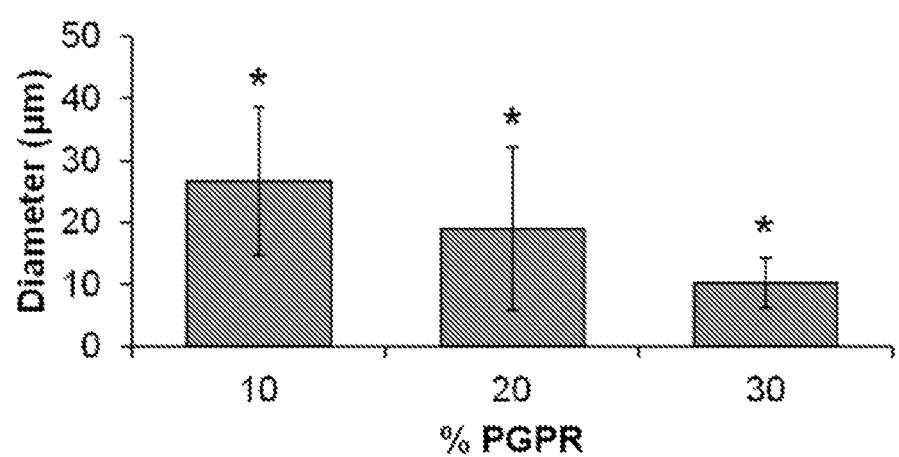
FIG. 10 illustrates a representative relationship between emulsifier concentration and pore size.

Represented porous microspheres are depicted in FIGS. 8A to 8C. Their pore shape and architecture were affected independent of overall pore size, shape and diameter. While the size and shape are generally determined as described above (e.g., needle diameter, tubing diameter, aqueous flow rate, emulsion ejection rate, pre-cure viscosity), morphology and pore dimensions can be manipulated by surfactant concentration, as depicted in FIG. 10. For example, for EGDMA, pore size decreased from an average of 20 micrometers to 5 micrometers when the emulsifier concentration (PGPR) increased from 10 wt. % to 30 wt. %. With decreasing pore size, the pore structure internally was also found to be more tortuous (a unit-less measure of path length compared to end-to-end distance for travel). Rapid freezing is likely better to prevent burst of the porous microparticles. Freeze drying is likely to prevent contained substance buildup near the particle surface, thereby allowing a slower release of any substance contained therein.

Polymerization of the continuous phase of the first component locked in the emulsion geometry and resulted in a high-porosity foam with an open-pore morphology. The average pore size, with PGPR as the emulsifier (in an amount from 10 wt. % to 30 wt. %) followed by polymerization occurring upon exposure to ultraviolet light, was from about 10 micrometer to about 30 micrometer (FIGS. 9A-9C), as depicted in the microparticles illustrated in FIGS. 8A-8C, respectively. Importantly, pore size may be controlled independent of microparticle size and vice versa. For example, pore size was altered to vary from 10 micrometer to 30 micrometer by simply decreasing the amount of emulsifier in the first component (e.g., from 30% PGPR to 10% PGPR, respectively) (FIG. 10). Thus, release rate of a substance held within the pores is readily adjusted as described herein.

In additional examples, HIPEs were prepared in first emulsions and comprised formulations that included a macromer (EGDMA) in amounts ranging from about 23.9 to 22.79 wt. %, an initiator (DMPA) in amounts ranging from about 0.47 to 0.49 wt. %, an emulsifier (PGPR) in amounts ranging from about 2.43 to 6.98 wt. % and water in amounts ranging from 69.77 to 73.17 wt. %. The double emulsion procedure and fabrication of microspheres was performed as described above.

In further examples, loaded microspheres were formed by a similar process described above, however, the first component comprised the stabilizing macromer (EGDMA, 500 mg with PGPR, 150 mg), a photoinitiator (DMPA, 10 mg) in the organic phase. While a biologic substance (recombinant human bone morphogenetic protein-2 (BMP-2), 5000 ng) in water (1.5 mL) was the aqueous phase. The two phases were mixed as described herein to form a first emulsion and then provided drop wise to a second component, thereby fabricating porous microspheres. In one example, these porous microspheres were formed to be about 800 micrometer in diameter. Loading efficiency of the BMP-2 was determined by crushing the microspheres and then incubating in 3 mL deionized water while agitating, for about 15 hours in small containers (e.g., 15 mL tubes). After agitation, the crushed particles were collected at a high speed in the incubating containers, the incubating liquid was removed and saved, and the particles were introduced to additional water as before. Protein concentrations in the collected liquids, when combined, was measured using a seven point calibration curve, and the amount encapsulated was compared to a theoretical maximum based on HIPE (or MIPE) concentration. It was found that the protein could be added to an aqueous phase and encapsulated without disrupting emulsion. The emulsion containing the encapsulated substance were formed into porous microspheres that were about 800 micrometer in diameter (on average) and had an average pore size of 14 micrometers. The protein encapsulation had little effect on particle size and microarchitecture. The protein assay found that the encapsulation efficiency was 73%±3%. This is contrasted with prior methods (e.g., emulsion-solvent evaporations) that have an efficiency that is significantly lower, sometimes as low as 15%. Without being bound by theory, the increased encapsulation efficiency may be associated both with the physical entrapment of the molecules and possible adsorption onto the microsphere pore walls. It is considered that efficiency of encapsulation may be further improved by decreasing pore size, fabricating particles with a closed shell, and/or increasing the concentration of the external aqueous phase (second component). The process may also include steps that decrease rate of diffusion (e.g., lengthening path length), decreasing coefficient of diffusion, and/or decreasing the concentration gradient. The example is further evidence that not only small substances but large proteins may be encapsulated as described herein.

The lack of organic solvents (diluents) in the making of and in the described components that form the porous microspheres provided the advantage of preventing toxic leachables, especially those that could possibly denature and/or destroy a substance contained within said microspheres. As such, there should be little concern regarding biocompatibility when adding a substance with the described compositions.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to its advantage.

When values are given it is understood that any of said numeric value may be considered to be about said numeric value.

Whenever a numerical range of degree or measurement with a lower limit and an upper limit is disclosed, any number and any range falling within the range is also intended to be specifically disclosed. For example, every range of values (in the form "from a to b," or "from about a to about b," or "from about a to b," "from approximately a to b," and any similar expressions, where "a" and "b" represent numerical values of degree or measurement) is to be understood to set forth every number and range encompassed within the broader range of values, including the values "a" and "b" themselves. Terms such as "first," "second," "third," etc. may be arbitrarily assigned and are merely intended to differentiate between two or more components, parts, or steps that are otherwise similar or corresponding in nature, structure, function, or action. For example, the words "first" and "second" serve no other purpose and are not part of the name or description of the following name or descriptive terms. The mere use of the term "first" does not mean that there any "second" similar or corresponding components, parts, or steps. Similarly, the mere use of the word "second" does not mean that there be any "first" or "third" similar or corresponding component, part, or step. Further, it is to be understood that the mere use of the term "first" does not mean that the element or step be the very first in any sequence, but merely that it is at least one of the elements or steps. Similarly, the mere use of the terms "first" and "second" does not mean any sequence. Accordingly, the mere use of such terms does not exclude intervening elements or steps between the "first" and "second" elements or steps.

The foregoing description is of examples embodying, at least in part, certain teachings of the invention. The invention, as defined by the appended claims, is not limited to the described embodiments. Alterations and modifications to the disclosed embodiments may be made without departing from the invention. The meaning of the terms used in this specification are, unless expressly stated otherwise, intended to have ordinary and customary meaning and are not intended to be limited to the details of the illustrated structures or the disclosed embodiments. Although the foregoing description of embodiments have shown, described and pointed out certain novel features of the invention, it will be understood that various omissions, substitutions, and changes in the form of the detail as illustrated as well as the uses thereof, may be made by those skilled in the art, without departing from the scope of the invention. Particularly, it will be appreciated that the one or more embodiments may manifest itself in other configurations as appropriate for the end use of the material made thereby.

What is claimed is:

1. A method of making a double emulsion comprising:
   preparing by mechanical dispersion a first portion as a high internal phase emulsion, the first portion as the high internal phase emulsion comprising at least one biodegradable polymeric material and at least one cross-linking agent in an organic phase, and further comprising a chemical to prevent Ostwald ripening in an aqueous phase; and
   adding drop wise the first portion in a second portion to form a porous microparticle-like composition, the second portion being in an aqueous phase,
   wherein the aqueous phase of the first portion is encapsulated in the porous microparticle-like composition,
   wherein the biodegradable polymeric material comprises:
      a macromer having at least one end group selected from one or more of an acrylate and a methacrylate;
      one or more linkages in the macromer, the one or more linkages selected from one or more of an anhydride and an ester,
      wherein the biodegradable polymeric material has an octanol-water partition coefficient of between about 2 and about 8,
      wherein the biodegradable polymeric material has a viscosity of between about 0.08 cP and about 1000 cP;
   wherein the porous microparticle-like composition includes a porous region containing at least one substance selected to be one or more of compatible with a biologic system, and active in a biologic system,
   wherein the porous microparticle-like composition has a spherical shape and a cross sectional diameter that is of a generally uniform size, the cross-sectional diameter in a range from between about 20 micrometers and about 1000 micrometers, with a standard deviation that is not more than 50 micrometers when the cross-sectional diameter is greater than 300 micrometers, and
   wherein the first portion and the second portion are solvent free.

2. The method of claim 1, wherein the first portion further comprises in the aqueous phase a substance selected to be one or more of compatible with a biologic system, and active in a biologic system.

3. The method of claim 1, wherein the adding drop-wise the first portion is performed at a flow rate that is between about 0.1 to about 3 ml per hour.

4. The method of claim 1, further comprising initiating crosslinking after adding drop wise the first portion in the second portion.

5. The method of claim 1, wherein the cross sectional diameter of the porous microparticle-like composition is affected by any one or more of the group consisting of a rate of adding drop wise the first portion in the second component, viscosity of the first microparticle-like composition, a flow rate of the second portion, a diameter of a passage for adding drop wise the first portion, and characteristics of a path containing the second portion.

6. The method of claim 1, wherein the aqueous phase of the first portion is encapsulated in the porous microparticle-like composition prior to polymerization.

7. The method of claim 1, wherein the at least one biodegradable polymeric material is stabilized with a quantity of an emulsifier lacking hydrogen bond donors in its hydrophilic head region while having a hydrophilic-lipophilic balance in a range of between about 2 and about 9.

8. A composition comprising:
a structural matrix comprising:
  a biodegradable polymeric material, the biodegradable polymeric material comprising:
    a macromer having at least one end group selected from one or more of an acrylate and a methacrylate;
    one or more linkages in the macromer, the one or more linkages selected from one or more of an anhydride and an ester,
    wherein the biodegradable polymeric material has an octanol-water partition coefficient of between about 2 and about 8,
    wherein the biodegradable polymeric material has a viscosity of between about 0.08 cP and about 1000 cP;
  a cross-linking agent; and
  a porous region containing at least one substance selected to be one or more of compatible with a biologic system, and active in a biologic system,
  wherein the composition has a spherical shape and a cross sectional diameter that is of a generally uniform size, the cross-sectional diameter in a range from between about 20 micrometers and about 1000 micrometers, with a standard deviation that is not more than 50 micrometers when the cross-sectional diameter is greater than 300 micrometers.

9. The composition of claim 8, wherein the biodegradable polymeric material further comprises one or more of a surfactant and a wetting agent when formed.

10. The composition of claim 8, wherein structural matrix is formed from a solvent-free high internal phase emulsion in which the biodegradable polymeric material had a viscosity of about or less than about 150 cP when formed.

11. The composition of claim 8, wherein the composition is biodegradable when in the biologic system, releasing the at least one substance from the porous region into the biologic system.

12. The composition of claim 8, wherein the biodegradable polymeric material is stabilized with a quantity of an emulsifier lacking hydrogen bond donors in its hydrophilic head region while having a hydrophilic-lipophilic balance in a range of between about 2 and about 9.

13. The composition of claim 8, wherein the biodegradable polymeric material is stabilized with a quantity of an emulsifier comprising an amphiphilic surfactant having a polar, water-soluble head group attached to a nonpolar, water insoluble hydrocarbon chain.

14. The composition of claim 8, wherein the composition is introducible into the biological system orally, parenterally, intramuscularly, intravenously, by injection, or by inhalation.

15. The composition of claim 8, wherein the porous region includes a plurality of pores, and wherein the plurality of pores are interconnected.

16. The composition of claim 15, wherein an individual pore of the plurality of pores of the porous region has a size that ranges from about 1 micrometer to about 100 micrometers.

17. The composition of claim 8, wherein a first size of the composition is tunable, and wherein a second size of the porous region is tunable.

18. The composition of claim 8, the porous region containing at least one substance selected to be compatible with an environmental system.

19. The composition of claim 8, the porous region containing at least one substance selected to be compatible with a chemical system.

20. The composition of claim 8, the porous region containing at least one substance selected to be compatible with a physical system.

* * * * *